(12) United States Patent
Lee et al.

(10) Patent No.: US 11,931,446 B2
(45) Date of Patent: Mar. 19, 2024

(54) COMPOSITION FOR PROMOTING HAIR GROWTH

(71) Applicant: AMOREPACIFIC CORPORATION, Seoul (KR)

(72) Inventors: Yonghee Lee, Yongin-si (KR); Jaeyoung Ko, Yongin-si (KR); Sungyeon Cho, Yongin-si (KR); Hyoung June Kim, Yongin-si (KR); Heungsoo Baek, Yongin-si (KR); Seunghyun Shin, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 18/045,974

(22) Filed: Oct. 12, 2022

(65) Prior Publication Data
US 2023/0110353 A1   Apr. 13, 2023

(30) Foreign Application Priority Data

Oct. 13, 2021  (KR) ........................ 10-2021-0135571

(51) Int. Cl.
*A61K 8/60* (2006.01)
*A23L 33/105* (2016.01)
*A61Q 7/00* (2006.01)

(52) U.S. Cl.
CPC ............ *A61K 8/602* (2013.01); *A23L 33/105* (2016.08); *A61Q 7/00* (2013.01)

(58) Field of Classification Search
None
See application file for complete search history.

(56) References Cited

FOREIGN PATENT DOCUMENTS

| JP | 5597828 B2 | 10/2014 |
| JP | 5617110 B2 | 11/2014 |
| JP | 2015131788 | * 7/2015 |
| JP | 2015131788 A | * 7/2015 |
| KR | 10-2019-0091162 A | 8/2019 |

* cited by examiner

*Primary Examiner* — Nannette Holloman
(74) *Attorney, Agent, or Firm* — Merchant & Gould P.C.

(57) ABSTRACT

The present disclosure provides a composition for promoting hair growth including camellia kaempferol glycoside as an active ingredient. The composition for promoting hair growth according to an aspect of the present disclosure can promote hair growth by promoting the proliferation of hair follicle cells without side effects. In addition, the composition for promoting hair growth can promote hair growth and prevent hair loss by inhibiting the apoptosis of outer root sheath cells. Such a composition for promoting hair growth can be used as an external application to the skin, and can be used as a food, cosmetics or pharmaceutical composition.

11 Claims, 5 Drawing Sheets

Control    camellia kaempferol glycoside

COMPOSITION FOR PROMOTING HAIR GROWTH

CROSS REFERENCE TO RELATED APPLICATION

The present application claims priority to Korean Patent Application No. 10-2021-0135571, filed Oct. 13, 2021, the entire contents of which are hereby incorporated by reference.

BACKGROUND OF THE INVENTION

Field of the Invention

The present disclosure relates to a composition for promoting hair growth.

DESCRIPTION OF THE RELATED ART

Hairs are primarily responsible for a defense function to protect the scalp from external stimuli such as ultraviolet rays and are also responsible for an aesthetic function of expressing the external image. However in modern society, hair loss is frequently caused by natural factors such as environmental pollution and strong ultraviolet rays, or physiological factors such as stress and hormonal imbalance. Unlike the past when a phenomenon of hair loss limitedly occurred in adult males, the phenomenon of hair loss currently occurs regardless of sex and age. Therefore, materials for prevention and treatment of hair loss are urgently needed.

A hair follicle, a physiological organ that produces hair, repeats a hair cycle divided into an anagen phase in which hair is generated and the generated hair is actively grown during the postnatal development process, a catagen phase in which hair is degenerated, a telogen phase which is maintained until hair loss, and an exogen phase in which hair loss occurs, and is involved in hair growth, maintenance, and loss.

The exact cause of hair loss has not been fully elucidated so far, but as the cause, inhibition of proliferation or decreased function of dermal papilla cells related to the hair cycle regulation, abnormal hair cycle due to the action of male hormones, abnormal changes in hair cycle due to decreased blood flow to the scalp, drugs such as anticancer drugs, mental stress, physical stimulation, environmental pollution, etc. have been discussed.

It is known that dermal papilla cells, a type of specialized fibroblasts in a hair bulb, interact with various types of epithelial cells in the hair follicle and play an important role in the formation of hair follicle, hair regeneration and hair growth. Thus, the growth and proliferation of dermal papilla cells and the inhibition of their apoptosis are important targets for the development of drugs that maintain the anagen phase of hair and inhibit hair loss.

Minoxidil and finasteride, which are conventionally used as agents for promoting hair growth and treating hair loss, have side effects such as systemic hair growth and decreased sexual function, and the specific mechanism of action of minoxidil is also not clearly clarified. Therefore, there is a need to develop a biological material that promotes the proliferation of dermal papilla cells while having fewer side effects.

SUMMARY OF THE INVENTION

In one aspect, the present disclosure is to provide a composition for promoting hair growth In one aspect, the present disclosure provides a composition for promoting hair growth including camellia kaempferol glycoside as an active ingredient.

In an exemplary embodiment, the camellia kaempferol glycoside may be extracted from *Camellia japonica* seed cake, which is a waste resource discarded after extraction of *Camellia japonica* seed oil.

In an exemplary embodiment, a content of the camellia kaempferol glycoside may be 0.01 to 20 wt % based on a total weight of the composition.

In an exemplary embodiment, a dosage of the camellia kaempferol glycoside may be 1 to 10 mg/kg/day.

In an exemplary embodiment, the promotion of the hair growth may be due to a proliferation of a hair follicle cell.

In an exemplary embodiment, the hair follicle cell may be a dermal papilla cell.

In an exemplary embodiment, the promotion of the hair growth may be due to inhibition of apoptosis of an outer root sheath cell.

In an exemplary embodiment, the composition may be a composition for external application to a skin.

In an exemplary embodiment, the composition may be a food composition, a cosmetic composition, or a pharmaceutical composition.

In one aspect, the composition for promoting hair growth according to the present disclosure has excellent hair growth promoting efficacy and can prevent hair loss.

In one aspect, the composition for promoting hair growth according to the present disclosure can promote the proliferation of hair follicle cells and can promote hair growth.

In one aspect, the composition for promoting hair growth according to the present disclosure can promote hair growth by inhibiting apoptosis of outer root sheath cells.

DETAILED DESCRIPTION OF THE INVENTION

Figure 1:
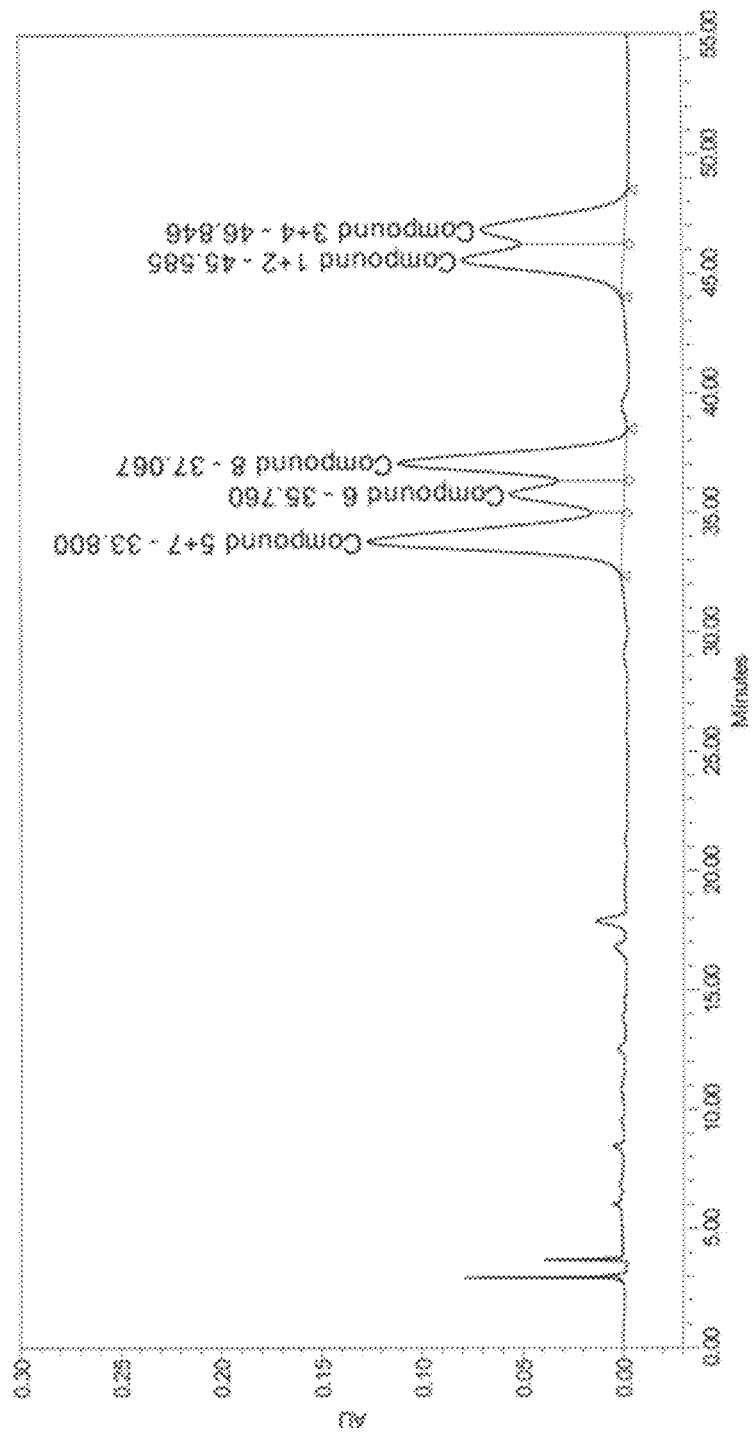
FIG. 1 is a chromatography analysis result of camellia kaempferol glycoside according to an embodiment of the present disclosure.

Hereinafter, the present disclosure will be described in detail.

In one aspect, the present disclosure provides a composition for promoting hair growth including camellia kaempferol glycoside as an active ingredient.

In the present disclosure, camellia refers to a *Camellia japonica* which is an evergreen tree in Theaceae plants, and is mainly distributed in East Asia including Korea. Camellia oil is extracted from camellia seeds, and the wood is used for furniture and handicrafts. In the present disclosure, all parts of the plant such as the root, stem, leaf, flower, etc. of the camellia can be used, and it can also be used as a whole plant (outpost).

In the present disclosure, the camellia kaempferol glycoside is a kaempferol glycoside derived from camellia, and can be prepared by extracting the extract from the camellia using a solvent and removing impurities, sugars and proteins from the extract using an ion exchange resin, but the present disclosure is not limited thereto. This camellia kaempferol glycoside may not contain a saponin component.

In one embodiment, the camellia kaempferol glycoside may be extracted from *Camellia japonica* seed cake, which is a waste resource discarded after extraction of *Camellia japonica* seed oil.

In one embodiment, the solvent may be water, an organic solvent, or a mixture thereof. The organic solvent may include, but is not limited to, $C_1$-$C_6$ alcohol, acetone, hexane, ethyl acetate, carbon dioxide, or a mixed organic solvent thereof.

In one embodiment, the camellia kaempferol glycoside may include at least one selected from the group consisting of camellia kaempferol triglycoside and camellia kaempferol tetraglycoside.

In one embodiment, the camellia kaempferol triglycoside may include at least one selected from the group consisting of a compound 1 of Formula 1, a compound 2 of Formula 2, a compound 3 of Formula 3, and a compound 4 of Formula 4.

[Formula 1]

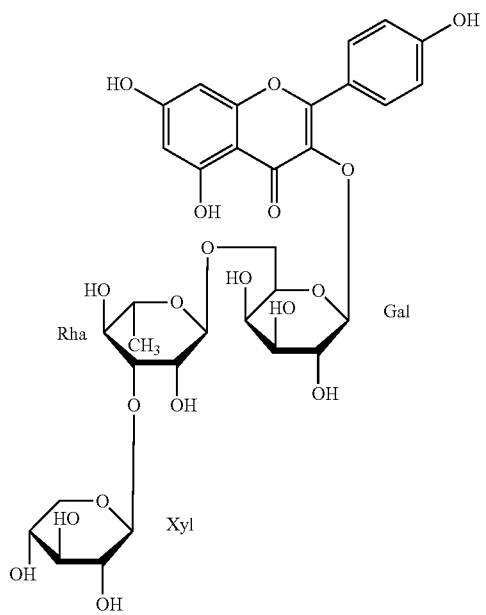

[Formula 2]

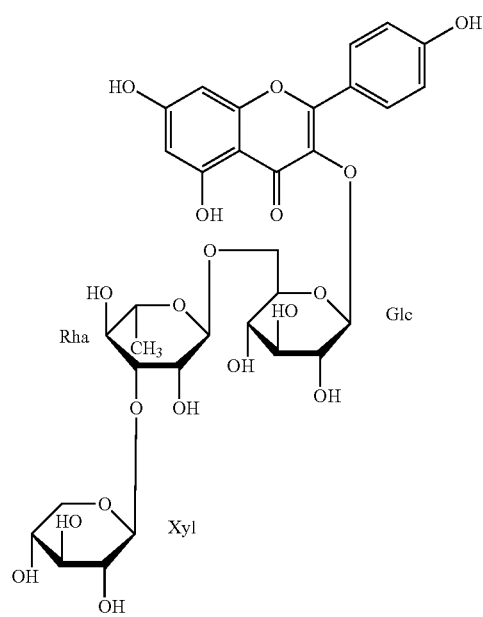

[Formula 3]

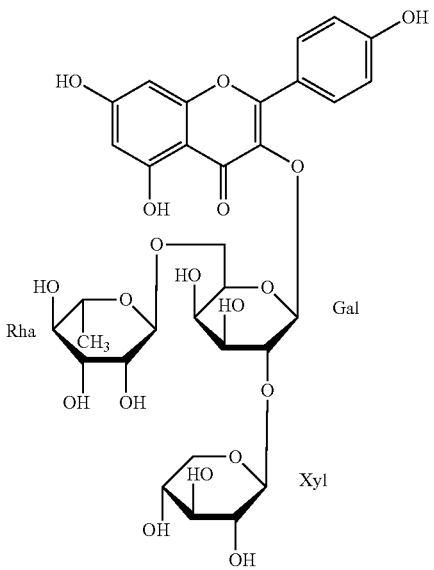

[Formula 4]

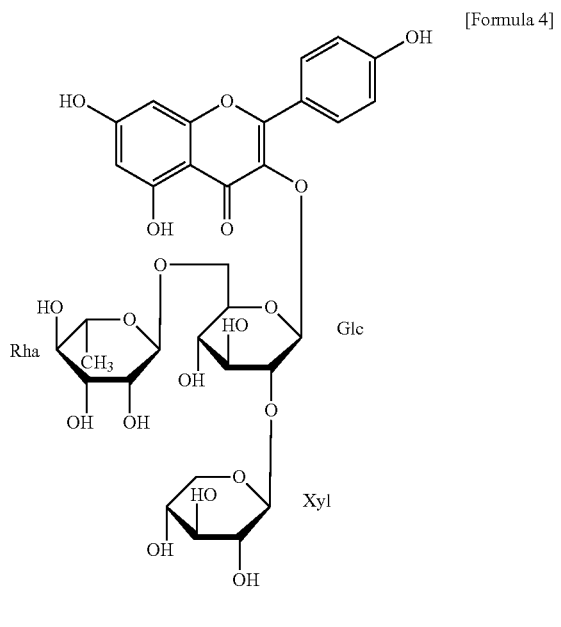

[Formula 6]

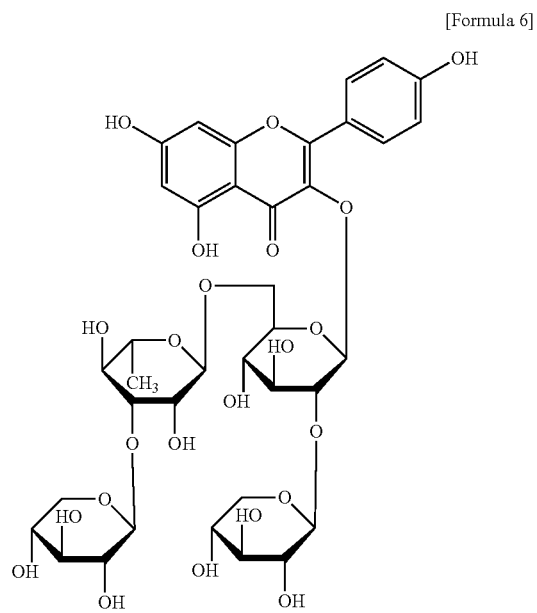

In one embodiment, the compound 1 may be Kaempherol-3-O-β-D-xylopyranosy(1→3)-O-α-L-rhamnopyranosyl(1→6)-O-β-D-galactopyranoside. The compound 2 may be Tsubakioside A. The compound 3 may be Kaempherol-3-O-α-L-rhamnopyranosyl(1→6)-O-β-D-xylopyranosyl-(1→2)-O-β-D-galactopyranoside. The compound 4 may be Camelliaside B.

In one embodiment, the camellia kaernpferol tetraglycoside may include at least one selected from the group consisting of a compound 5 of Formula 5, a compound 6 of Formula 6, a compound 7 of Formula 7, and a compound 8 of Formula 8.

[Formula 5]

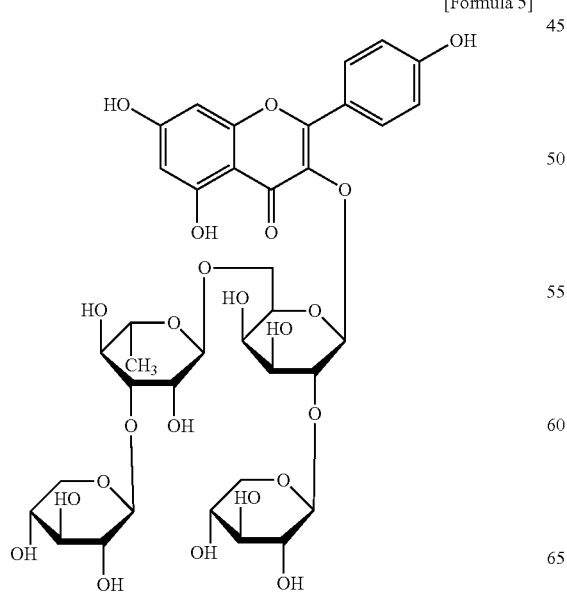

[Formula 7]

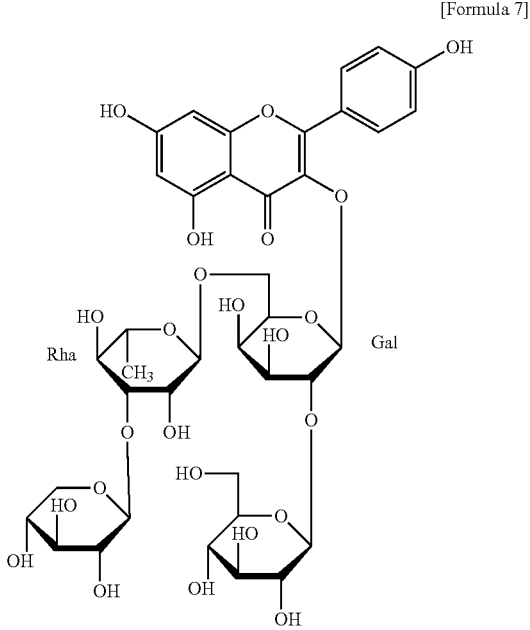

-continued

[Formula 8]

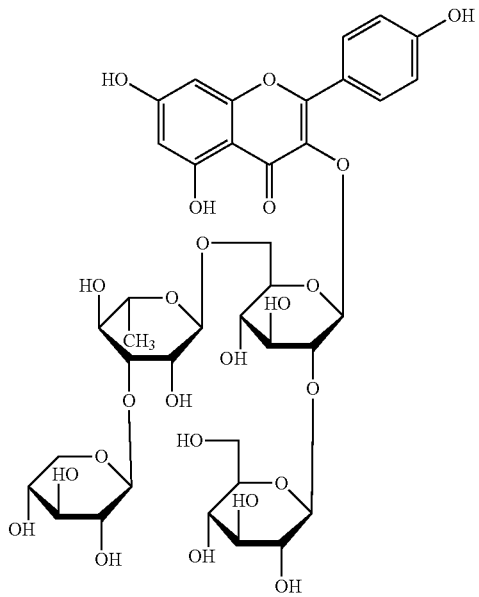

In one embodiment, the compound 5 may be Tsubakioside C. The compound 6 may be Tsubakioside B. The compound 7 may be Tsubakioside D. The compound 8 may be Kaempherol-3-O-β-D-xylopyranosyl(1→3)-O-α-L-rhamnopyranosyl(1→6)-O-β-D-galactopyanosyl-(1→2)-O-β-D-glucopyranoside.

In one embodiment, a weight ratio of the camellia kaempferol triglycoside and the camellia kaempferol tetraglycoside may be 1:1 to 2. For example, a weight ratio of the camellia kaempferol triglycoside and the camellia kaempferol tetraglycoside may be 1:1 to 2, 1:1.2 to 2, 1:1.4 to 2, 1:1.4 to 1.8, or 1:1.6 to 1.8.

In one embodiment, the content of the camellia kaempferol glycoside may be 0.01 to 20 wt % based on the total weight of the composition. If the content of camellia kaempferol glycoside is less than 0.01 wt %, the hair growth promoting efficacy is lowered, and if the content of camellia kaempferol glycoside is more than 20 wt %, irritation to the scalp may be severe. Specifically, the content of the camellia kaempferol glycoside is 0.01 wt % or more, 0.02 wt % or more, 0.03 wt % or more, 0.04 wt % or more, 0.05 wt % or more, 0.1 wt % or more, 0.2 wt % or more, 0.3 wt % or more, 0.4 wt % or more, 0.5 wt % or more, 0.6 wt % or more, 0.7 wt % or more, 0.8 wt % or more, 0.9 wt % or more, 1 wt % or more, 1.5 wt % or more, 2 wt % or more, 2.5 wt % or more, 3 wt % or more, 3.5 wt % or more, 4 wt % or more, 4.5 wt % or more or 5 wt % or more; but 20 wt % or less, 19.5 wt % or less, 19 wt % or less, 18.5 wt % or less, 18 wt % or less, 17.5 wt % or less, 17 wt % or less, 16.5 wt % or less, 16 wt % or less, 15.5 wt % or less, or 15 wt % or less, based on the total weight of the composition.

In one embodiment, the camellia kaempferol glycoside may be administered at a dosage of 1 to 10 mg/kg/day. If the dosage of camellia kaempferol glycoside is less than 1 mg/kg/day, the hair growth promoting efficacy is lowered, and if the dosage of camellia kaempferol glycoside exceeds 10 mg/kg/day, skin irritation may be severe. Particularly, the dosage of camellia kaempferol glycoside may be 1 mg/kg/day or more, 1.1 mg/kg/day or more, 1.2 mg/kg/day or more, 1.3 mg/kg/day or more, 1.4 mg/kg/day or more, 1.5 mg/kg/day or more, 1.6 mg/kg/day or more, 1.7 mg/kg/day or more, 1.8 mg/kg/day or more, 1.9 mg/kg/day or more, 2 mg/kg/day or more, 2.1 mg/kg/day or more, 2.2 mg/kg/day or more, 2.3 mg/kg/day or more, 2.4 mg/kg/day or more, 2.5 mg/kg/day or more, 2.6 mg/kg/day or more, 2.7 mg/kg/day or more, 2.8 mg/kg/day or more, 2.9 mg/kg/day or more, 3 mg/kg/day or more, 3.1 mg/kg/day or more, 3.2 mg/kg/day or more, 3.3 mg/kg/day or more, 3.4 mg/kg/day or more or 3.5 mg/kg/day or more; but, 10 mg/kg/day or less, 9.9 mg/kg/day or less, 9.8 mg/kg/day or less, 9.7 mg/kg/day or less, 9.6 mg/kg/day or less, 9.5 mg/kg/day or less, 9.4 mg/kg/day or less, 9.3 mg/kg/day or less, 9.2 mg/kg/day or less, 9.1 mg/kg/day or less, 9 mg/kg/day or less, 8.9 mg/kg/day or less, 8.8 mg/kg/day or less, 8.7 mg/kg/day or less, 8.6 mg/kg/day or less, 8.5 mg/kg/day or less, 8.4 mg/kg/day or less, 8.3 mg/kg/day or less, 8.2 mg/kg/day or less, 8.1 mg/kg/day or less, 8 mg/kg/day or less, 7.5 mg/kg/day or less or 7 mg/kg/day or less.

In one embodiment, the hair growth may be promoted by promoting the proliferation of hair follicle cells. The hair follicle cells may be dermal papilla cells. The dermal papilla cells of hair follicle interact with various types of epithelial cells in hair follicles and play an important role in hair follicle formation, hair regeneration, and hair growth. The composition according to the present disclosure can promote the proliferation of dermal papilla cells of hair follicle, thereby promoting hair growth and preventing hair loss.

In one embodiment, the promotion of hair growth may be due to inhibition of apoptosis of an outer root sheath cell. The outer root sheath cell protects the hair generated in the hair bulb until complete keratinization and transports it to the epidermis. The composition according to the present disclosure can inhibit the apoptosis of the outer root sheath cell and promote hair growth.

In one embodiment, the route of administration of the composition is not limited, but may be transdermally or externally applied to the skin.

In an embodiment, the composition may be a cosmetic composition. The cosmetic composition may be formulated, for example, into a softening lotion, an as ring lotion, a nourishing lotion, a nourishing cream, a massage cream, an eye cream, an eye essence, an essence, a cleansing cream, a cleansing lotion, a cleansing foam, a cleansing water, a pack, a powder, a body lotion, a body cream, a body essence, a body cleanser, a hair dye, a shampoo, a rinse, a hair fixative, a hair tonic, an ointment, a gel, a cream, a patch, a spray, a powder, a akin adhesive, etc., although not being limited thereto.

In addition, each formulation may contain, in addition to the essential ingredient described above, other ingredients, that may be selected by those skilled in the art without difficulty depending on the type of the formulation, purpose of use, etc.

The cosmetic composition may be provided as any topically applicable formulation. For example, it may be provided as a solution, an emulsion obtained by dispersing an oil phase in an aqueous phase, an emulsion obtained by dispersing an aqueous phase in an oil phase, a suspension, a solid, a gel, a powder, a paste, a microneedle, a foam or an aerosol. These formulations may be prepared according to common methods in the art.

The cosmetic composition according to the present disclosure may further contain functional additives and ingredients contained in general cosmetic compositions in addition to the compound of the present disclosure. The functional additive may include an ingredient selected from a group consisting of a water-soluble vitamin, an oil-soluble vitamin, a polypeptide, a polysaccharide, a sphingolipid and a seaweed extract. The cosmetic composition according to the present disclosure may further contain another ingredient that can provide synergistic effect to the main effect within a range not negatively affecting the main effect. In addition, the cosmetic composition according to the present disclosure may further contain a wetting agent, an emollient, a surfactant, a UV absorbent, an antiseptic, a sterilizer, an antioxidant, a pH control agent, an organic or inorganic pigment, a flavor, a cooling agent or an antiperspirant. The mixing amount of the ingredient may be easily determined by those skilled in the art within a range not negatively affecting the purpose and effect of the present disclosure. The mixing amount may be 0.001 to 10 wt %, specifically 0.01 to 3 wt %, based on the total weight of the composition.

In an embodiment, the composition may be a food composition. The food composition may be formulated into, for example, a tablet, a granule, a pill, a powder, a liquid such as a drink, a caramel, a gel, a bar, a tea bag, etc., although not being specially limited thereto. Each formulation may contain ingredients commonly used in the art that may be selected by those skilled in the art without difficulty depending on the type of the formulation, purpose of use, etc. in addition to the active ingredient, A synergistic effect may be achieved with the active ingredient is used together with other ingredients.

In an embodiment, the food composition may contain various nutrients, vitamins, minerals (electrolytes), flavorants such as synthetic flavorants or natural flavorants, colorants, extenders (cheese, chocolate, etc.), pectic acid and its salts, alginic acid and its salts, organic acids, protective colloidal thickeners, pH control agents, stabilizer, antiseptic, glycerin, alcohols, carbonating agents used in carbonated beverages, etc. In addition, the food composition according to an embodiment may further contain a pulp for preparation of a natural fruit juice, a fruit juice beverage or a vegetable beverage. These ingredients may be used either alone or in combination. The content of these additives is of no great importance. In general, they are contained within a range of about 0 to 50 parts by weight based on 100 parts by weight of the composition according to an embodiment.

In an embodiment, the composition may be a pharmaceutical composition. The pharmaceutical composition may be administered orally, parenterally, rectally, topically, transdermally, intravenously, intramuscularly, intraperitoneally, subcutaneously, etc. Formulations for oral administration may include a tablet, a pill, a soft or hard capsule, a granule, a powder, a fine granule, a liquid, an emulsion or a pellet, although not being limited thereto. Formulations for parenteral administration may include a solution, a suspension, an emulsion, a gel, an injection, a medicinal drip, a suppository, a patch or a spray, although not being limited thereto. The formulations may be prepared easily by common methods in the art and may further contain a surfactant, an excipient, a wetting agent, an emulsification accelerator, a suspending agent, a salt or a buffer for control of osmotic pressure, a colorant, a flavor a stabilizer, an antiseptic, a preservative or other commonly used adjuvants.

In one aspect, the present disclosure provides a method for promoting hair growth or preventing hair loss, including the step of administering a composition including an effective amount of camellia kaempferol glycoside to a subject in need of promoting hair growth or preventing hair loss. In one aspect, the administration of the method may be performed according to the administration method and administration dose described in the present disclosure.

In one aspect, the present disclosure provides the use of camellia kaempferol glycoside for preparing a composition for promoting hair growth.

In one aspect, the present disclosure provides the use of camellia kaempferol glycoside for promoting hair growth.

Hereinafter, the present disclosure will be described in detail through examples, etc. However, the following examples are for illustrative purposes only and it will be obvious to those having ordinary skill in the art that the scope of the present disclosure is not limited by the examples.

[Experimental Example 1] Preparation of Camellia Kaempferol Glycoside 1 kg of *Camellia japonica* seed cake (Jeju Island) was milked at low temperature to remove oil, and 8 kg of 70% ethanol was added. Extraction was performed at 60° C., for 8 hours using a warm extractor and filtering was performed with a filter press to obtain a *Camellia japonica* seed cake extract. The *Camellia japonica* seed cake extract was concentrated under reduced pressure at 50 to 60° C., with a rotary vacuum concentrator until a solid content was about 50% to obtain 200 g of a concentrated solution. The concentrate was diluted with purified water so as to have the solid content of 10%. After loading this solution into a glass tube column filled with 2 L of ion exchange resin (HP-20), it was washed with 10 L of purified water to remove impurities, sugars, and proteins, and then 10 L of 30% ethanol was flowed to obtain an eluate. The eluate was concentrated under reduced pressure and freeze-dried to obtain 20 g of camellia kaempferol glycoside powder. The thus obtained camellia kaempferol glycoside powder was dissolved in 70% ethanol and fractionated by a reverse phase chromatography under the condition of 0.1% TFA water/ 0.1% TFA acetonitrile to separate the components contained in each batch. The separated components were the compounds 1 to 4, which were camellia kaempferol triglycosides, and the compounds 5 to 8, which were camellia kaempferol tetraglycosides. The compounds 1 to 8 were found to have structures of Formulas 1 to 8, respectively. The results of the reverse phase chromatography were shown in Table 1 and FIG. 1.

[Formula 1]
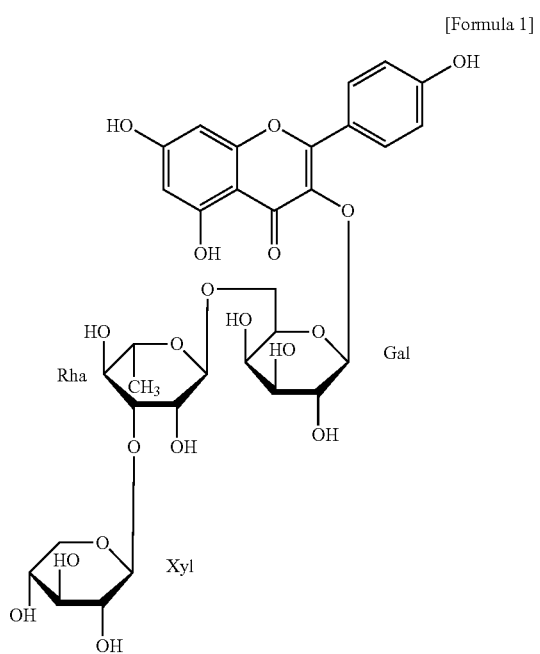
[Formula 2]
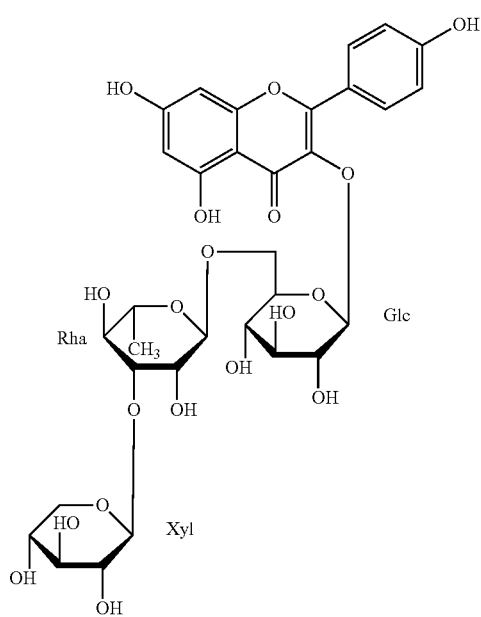
[Formula 3]
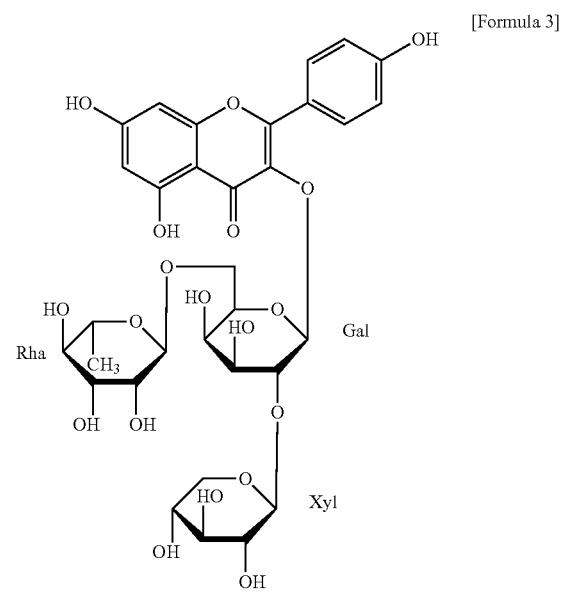
[Formula 4]
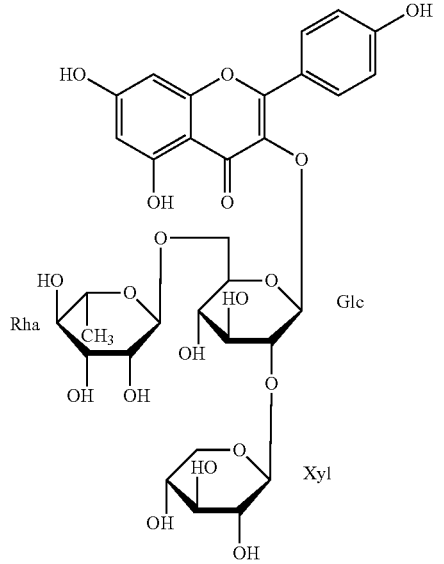

[Formula 5]

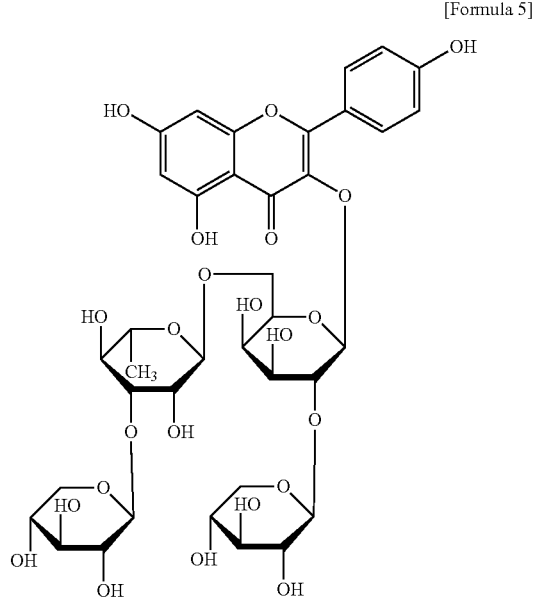

[Formula 6]

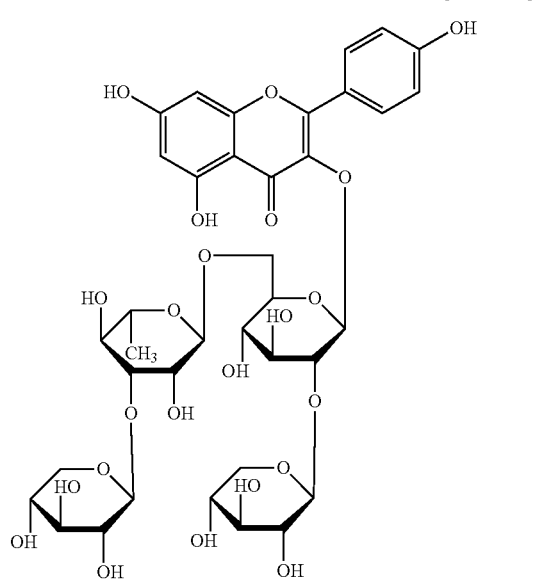

[Formula 7]

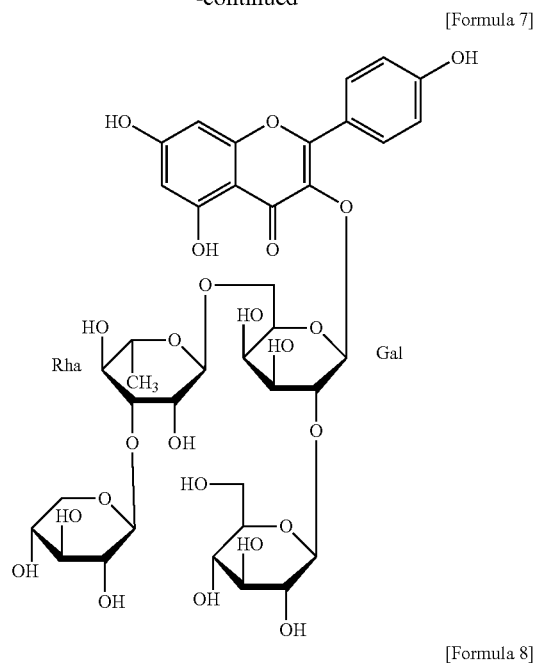

[Formula 8]

TABLE 1

|  | Retention time (min) | Area (%) |
| --- | --- | --- |
| Compound 5 + Compound 7 | 33.800 | 28.99 |
| Compound 6 | 35.760 | 11.13 |
| Compound 8 | 37.067 | 23.28 |
| Compound 1 + Compound 2 | 45.585 | 18.92 |
| Compound 3 + Compound 4 | 46.846 | 17.67 |

[Experimental Example 2] Efficacy Evaluation of Promoting the Proliferation of Dermal Papilla Cell of Hair Follicle The dermal papilla cells of hair follicle were isolated from a human occipital scalp tissue using a microscope and cultured for 14 days in a culture dish coated with collagen type I. After culturing the culture medium having the DMEM (Dulbecco's modified eagles medium; HyClone GE Healthcare) containing antibiotics (1%), fungizone (0.1%), and 20% FBS at the conditions of 5% $CO_2$, 37° C. for 72 hours, the medium was replaced with the DMEM medium containing 10% FBS. Then, when the cells grew over 90% of the dish, the cultured cells were collected using 0.25% trypsin/10 ml/10 EDTA (Welgene). The DMEM medium containing 10% FBS was cultured at 5% $CO_2$, 37° C. for 72 hours (until the cells grew to more than 90% of the dish), which was used for subsequent experiments.

Figure 2:
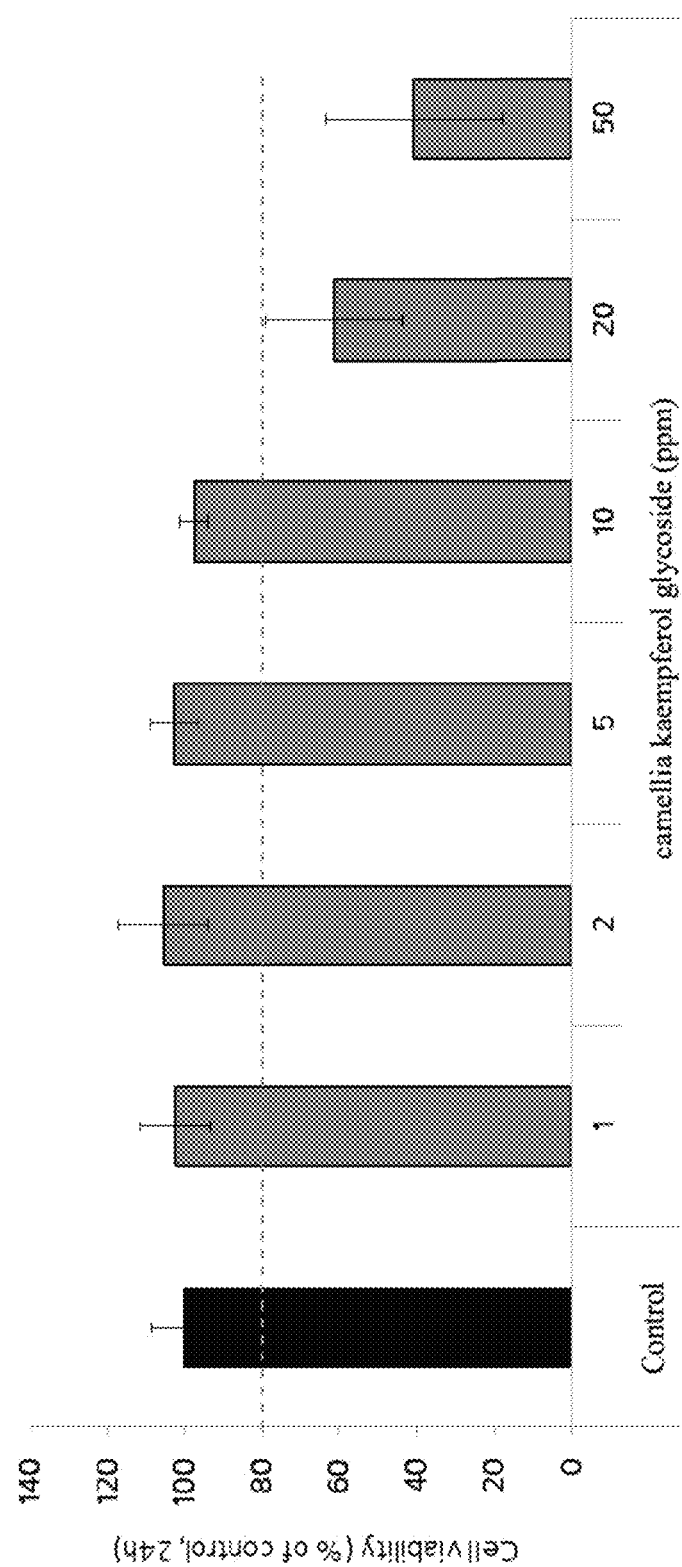
FIG. 2 is a graph showing the promoting efficacy of the proliferation of dermal papilla cells by a composition for promoting hair growth according to an embodiment of the present disclosure.

The cultured dermal papilla cells were inoculated at a rate of 2000 cells/well in a 96-well plate, and then cultured at 5% $CO_2$, 37° C. for 24 hours. After the camellia kaempferol glycoside of Example 1 was treated by each concentration (1 ppm, 2 ppm, 5 ppm, 10 ppm, 20 ppm, 50 ppm), it was incubated at 5% $CO_2$, 37° C. for 72 hours. An untreated group was used as a control. After incubation with CCK-8 (DONGJIN) for 2 hours, an absorbance was measured at 450 nm using a microplate reader. By setting the value of the control to 100, a relative cell viability was converted through the measured absorbance and shown in FIG. 2.

[Experimental Example 3] Efficacy Evaluation of Inhibiting Apoptosis of Outer Root Sheath Cells The outer root sheath cells were isolated from human occipital scalp tissues using a microscope and cultured in a culture dish coated with collagen type I for 14 days. After culturing the culture medium having the DMEM (Dulbecco's modified eagles medium; HyClone GE Healthcare) containing antibiotics (1%), fungizone (0.1%), and 20% FBS at the conditions of 5% $CO_2$, 37° C. for 72 hours, the medium was replaced with the epilife medium containing EDGS. When the cells grew over 90% of the dish, the cultured cells were collected using 0.25% trypsin/10 mM EDTA (Welgene), put in the epilife medium containing EDGS, and cultured at 5% $CO_2$, 37° C. for 72 hours (until cells have grown to more than 90% of the dish), which were used for subsequent experiments.

Figure 3:
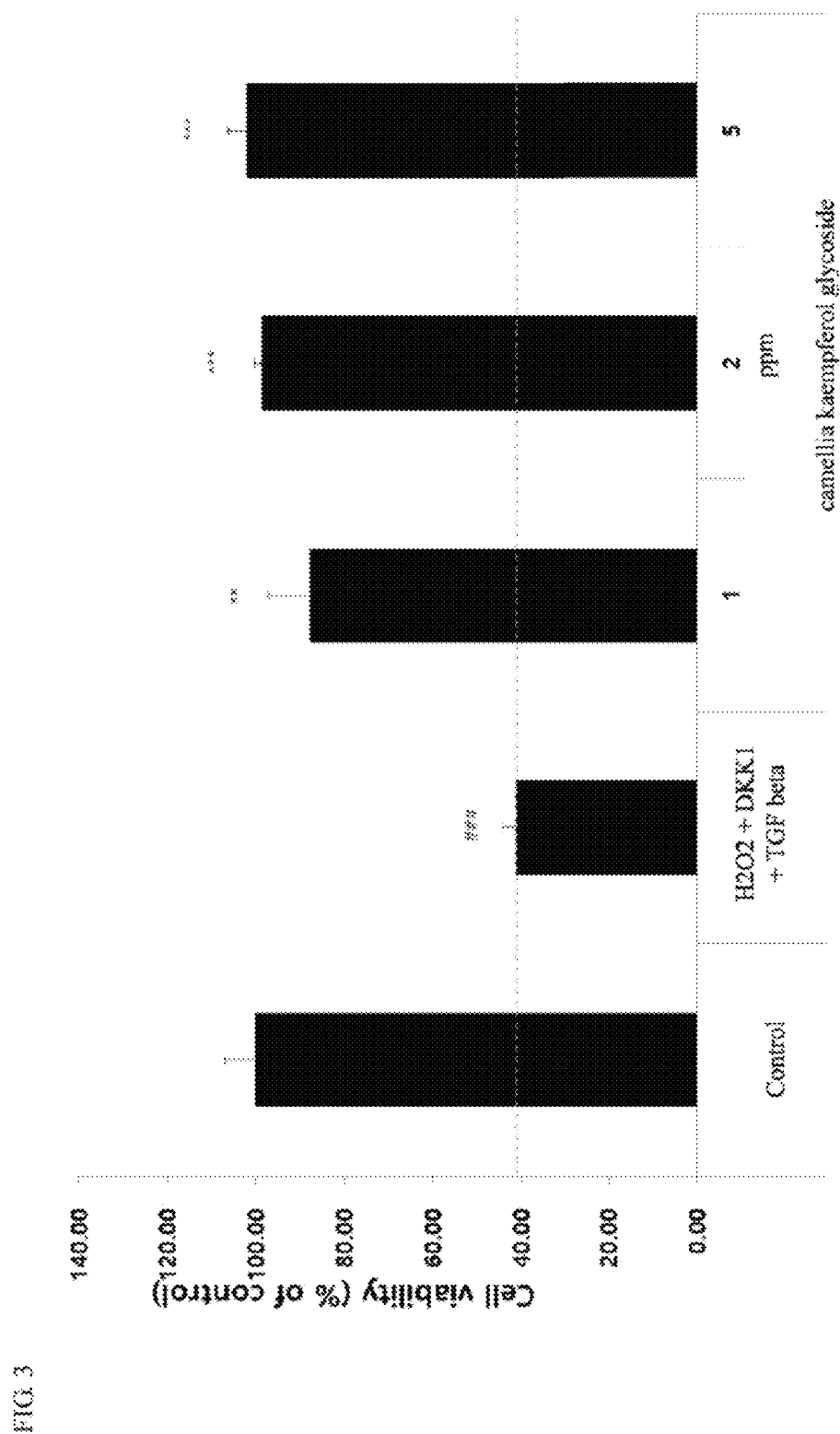
FIG. 3 is a graph showing the inhibiting efficacy of apoptosis of outer root sheath cells by a composition for promoting hair growth according to an embodiment of the present disclosure.

After the camellia kaempferol glycoside of Example 1 was treated for 4 hours by concentration (1 ppm, 2 ppm, 5 ppm), DKK1, H2O2, TGF beta 2, known as hair loss inducing factors, were additionally added and cultured overnight. After incubation with CCK-8 (DONGJIN) for 2 hours, absorbance was measured at 450 nm using a microplate reader. By setting the value of the control to 100, the relative cell viability was converted through the measured absorbance and shown in FIG. 3. The control represents the group not treated with anything

[Experimental Example 4] Antioxidative Activity Evaluation in Outer Root Sheath Cells After the outer root sheath cells cultured for the experiment in Experimental Example 2 were inoculated on an 8-chamber slide by 10000 cells/well, they were cultured at 5% $CO_2$, 37° C. for 24 hours. After treatment with the camellia kaempferol glycoside (5 ppm) of Example 1, the cell culture medium solution was removed at the end of additional incubation, and formalin solution was added to be immobilized for at least 15 minutes at room temperature. The immobilization solution was removed and washed 3 times for 3 minutes with a washing buffer (0.1% BSA in PBS). After standing at room temperature for 30 minutes with a permeabilization solution, it was reacted at room temperature for 30 to 60 minutes with a blocking buffer (0.1 to 1% BSA in PBS). The antibody for a target protein (NRF2) was diluted in the blocking buffer and left at 4° C. overnight. After bringing it to room temperature, a primary antibody solution was removed and washed 4 times for 3 minutes with the washing buffer (0.1% BSA in PBS). A secondary antibody (fluorescent dye bound) capable of targeting the primary antibody was diluted in the blocking buffer and reacted at room temperature for 2 hours. After that, a mounting solution was applied to the reactant, and a cover glass was placed to prevent bubbles from forming. The result was observed under a fluorescence microscope and shown in FIG. 4. As a control group, an untreated group was used.

Figure 4:
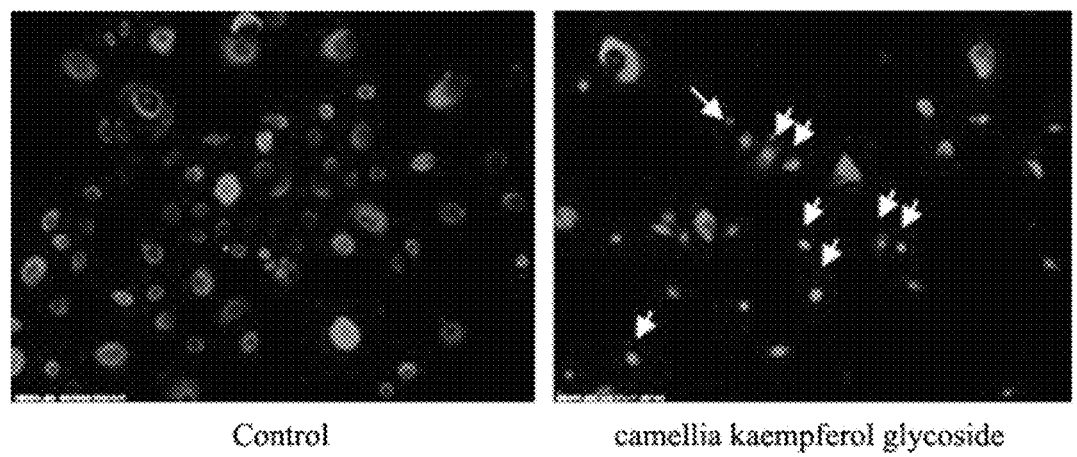
FIG. 4 is a graph showing the antioxidative activity in outer root sheath cells by a composition for promoting hair growth according to an embodiment of the present disclosure.

As can be seen from FIG. 4, it was confirmed that NRF2 protein, known as an antioxidant index when treated with the camellia kaempferol glycoside (0.1 Invest Dermatol. 2017 February; 137(2): 295-304, Oxidative Damage Control in a Human (Mini-) Organ): Nrf2 Activation Protects against Oxidative Stress-Induced Hair Growth Inhibition), moved into the nucleus of the outer root sheath cells (the arrow in FIG. 4 indicated that the NRF2 protein moved into the nucleus). Through this, it was found that the camellia kaempferol glycoside could inhibit the apoptosis of the outer root sheath cells.

[Experimental Example 5] Evaluation of Growth Efficacy of Hair Follicle Length

Figure 5:
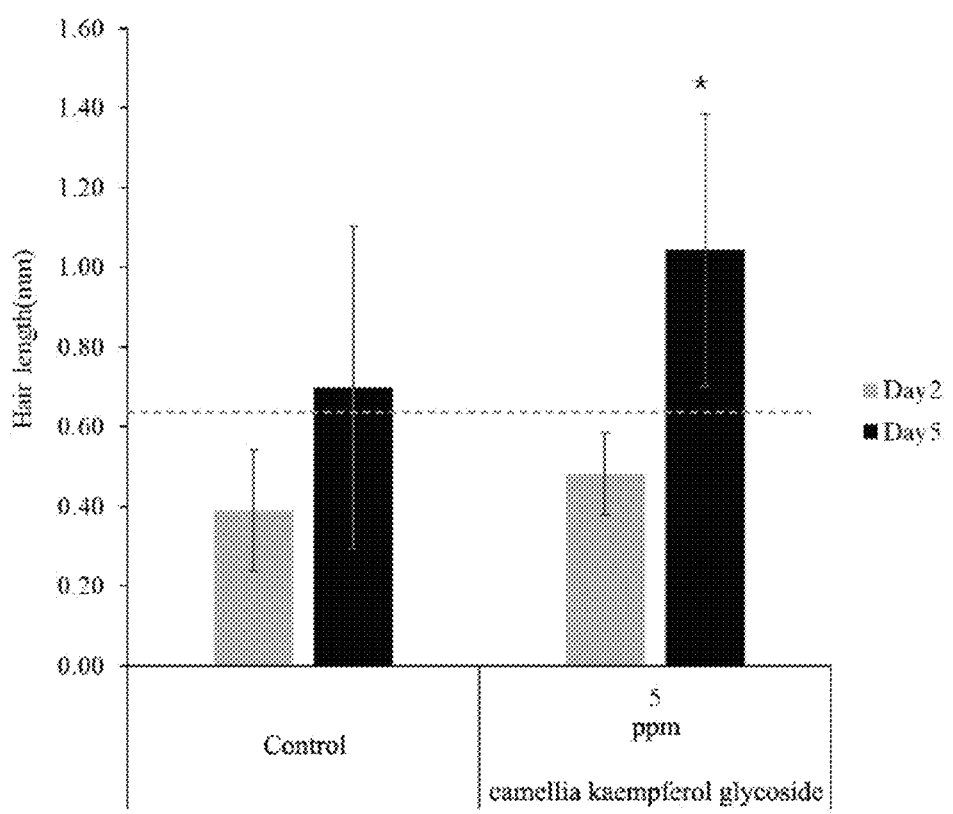
FIG. 5 is a graph showing the results of hair growth by a composition for promoting hair growth according to an embodiment of the present disclosure.
Figure 6:
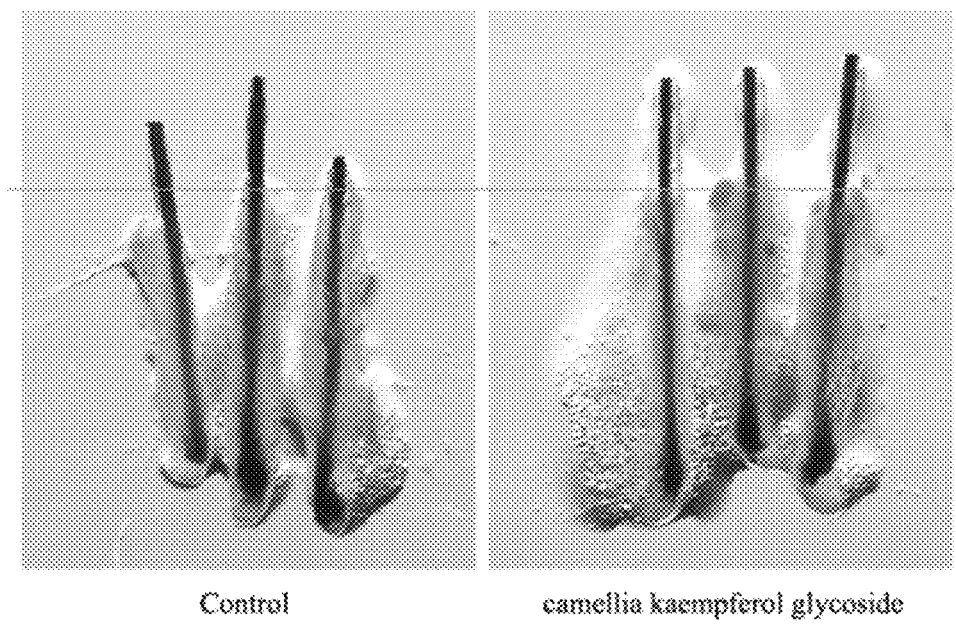
FIG. 6 is a photograph showing the results of hair growth by a composition for promoting hair growth according to an embodiment of the present disclosure.

Twenty hair follicle samples per a group for experimental application were isolated from a 57-year-old female. The isolated hair follicle samples were cultured on 500 ul of E medium containing 2 mM L-glutamine, 10 ng/ml hydrocortisone, 1% antibiotics, and 0.1% fungizone, in a 24-well plate by 6 per each well. Camellia saponin B1 (0.1 ppm), camellia saponin B2 (0.1 ppm) and Example 2 (0.01 ppm, 0.1 ppm) were treated in the 24-well plate. A sample untreated was used as a control. The medium was changed every 2 to 3 days. The length of hair growth was measured on the 2nd and 5th days and shown in FIG. 5, and on the 7th day, hair follicles were photographed using a stereomicroscope (Dongwon CNS, Korea) and shown in FIG. 6.

[Formulation Example 1] Soap

A soap was prepared with the composition shown in Table 3 below according to a commonly employed method.

TABLE 2

| Ingredients | Contents |
|---|---|
| Camellia kaempferol glycoside of Example 1 | 1.5 g |
| Titanium dioxide | 0.5 g |
| Polyethylene glycol | 1 g |
| Glycerin | 0.5 g |
| Ethylenediaminetetraacetic acid | 0.5 g |
| Sodium | 1 g |
| Pigment | 0.2 g |
| Soap scent | 0.2 g |
| Soap base | 94.1 g |

[Formulation Example 2] Liquid Ampoule

A liquid ampoule was prepared with the composition shown in Table 4 below according to a commonly employed method.

TABLE 3

| Ingredients | Contents |
| --- | --- |
| Camellia kaempferol glycoside of Example 1 | 50 mg |
| Indigestible maltodextrin | 100 mg |
| Citric acid | 10 mg |
| Flavor | 5 mg |
| Purified water | 28.5 g |

[Formulation Example 3] Cream

A cream was prepared with the composition shown in Table 5 below according to a commonly employed method.

TABLE 4

| Ingredients | Contents |
| --- | --- |
| Camellia kaempferol glycoside of Example 1 | 3 g |
| Polyethylene glycol monostearate | 4 g |
| Self-emulsifying glyceryl monostearate | 10 g |
| Cetyl alcohol | 8 g |
| squalene | 10 g |
| tri2-ethyl hexane glyceryl | 10 g |
| Sphingoglycolipid | 2 g |
| 1,3-butylene glycol | 14 g |
| Purified water | 189 g |

[Formulation Example 4] Cosmetic Liquid Formulation

A cosmetic liquid formulation was prepared with the composition shown in Table 6 below according to a commonly employed method.

TABLE 5

| Ingredients | Contents |
| --- | --- |
| Camellia kaempferol glycoside of Example 1 | 3 g |
| Hydroxyethylene cellulose | 15 g |
| Xanthan gum | 4 g |
| 1,3-butylene glycol | 10 g |
| Glycerin | 8 g |
| Sodium hyaluronate | 5 g |
| Purified water | 155 g |

[Formulation Example 5] Soft Capsule 60 mg of camellia kaempferol glycoside of Example 1, 160 mg of L-carnitine, 320 mg of soybean oil, 2 mg of palm oil, 8 mg of hydrogenated vegetable oil, 4 mg of yellow wax and 6 mg of lecithin were mixed, and filled into one capsule according to a commonly employed method to prepare a soft capsule.

[Formulation Example 6] Tablet 60 mg of camellia kaempferol glycoside of Example 1, 500 mg of galacto-oligosaccharide, 80 mg of lactose, and 220 mg of maltose were mixed and granulated using a fluidized bed dryer. Then, 6 mg of sugar ester was added and compressed with a tablet press to prepare tablets.

[Formulation Example 7] Granule 60 mg of camellia kaempferol glycoside of Example 1, 250 mg of anhydrous crystalline glucose, and 550 mg of starch were mixed, granulated using a fluidized bed granulator, and filled a bag to prepare granules.

[Formulation Example 8] Drink Beverage 60 mg of the camellia kaempferol glycoside of Example 1, 10 g of glucose, 0.6 g of citric acid, and 25 g of liquid oligosaccharide were mixed, and then 500 ml of purified water was added to the mixture. After filling each bottle with 200 ml of the mixture, the bottle was sterilized at 130° C. for 4 to 5 seconds to prepare a drink beverage.

What is claimed is:

1. A method for promoting hair growth or preventing hair loss, comprising the step of administering a composition comprising an effective amount of camellia kaempferol glycoside to a subject in need of promoting hair growth or preventing hair loss,
    wherein the camellia kaempferol glycoside is extracted from *Camellia japonica* seed cake.
2. The method according to claim 1, wherein the camellia kaempferol glycoside includes at least one selected from the group consisting of camellia kaempferol triglycoside and camellia kaempferol tetraglycoside.
3. The method according to claim 1, wherein a content of the camellia kaempferol glycoside is 0.01 to 20 wt % based on a total weight of the composition.
4. The method according to claim 1, wherein a dosage of the camellia kaempferol glycoside is 1 to 10 mg/kg/day.
5. The method according to claim 1, wherein the promotion of the hair growth is due to a proliferation of a hair follicle cell.
6. The method according to claim 5, wherein the hair follicle cell is a dermal papilla cell.
7. The method according to claim 1, wherein the promotion of the hair growth is due to inhibition of apoptosis of an outer root sheath cell.
8. The method according to claim 1, wherein the composition is a composition for external application to a skin.
9. The method according to claim 1, wherein the composition is a food composition.
10. The method according to claim 1, wherein the composition is a cosmetic composition.
11. The method according to claim 1, wherein the composition is a pharmaceutical composition.

* * * * *